United States Patent
Ke

(10) Patent No.: US 11,944,663 B2
(45) Date of Patent: Apr. 2, 2024

(54) METHOD FOR TREATING ANGIOGENIC EYE DISORDERS USING VEGF ANTAGONISTS

(71) Applicant: Chengdu Kanghong Biotechnologies Co. Ltd., Chengdu (CN)

(72) Inventor: Zunhong Ke, Chengdu (CN)

(73) Assignee: Chengdu Kanghong Biotechnologies Co. Ltd. (CN)

(*) Notice: Subject to any disclaimer, the term of this patent is extended or adjusted under 35 U.S.C. 154(b) by 213 days.

(21) Appl. No.: 17/351,723

(22) Filed: Jun. 18, 2021

(65) Prior Publication Data

US 2021/0393738 A1  Dec. 23, 2021

Related U.S. Application Data

(60) Provisional application No. 63/040,850, filed on Jun. 18, 2020.

(51) Int. Cl.
| | | |
|---|---|---|
| *A61K 38/17* | (2006.01) |
| *A61K 47/12* | (2006.01) |
| *A61K 47/18* | (2017.01) |
| *A61K 47/26* | (2006.01) |
| *A61K 47/68* | (2017.01) |
| *A61P 27/02* | (2006.01) |

(52) U.S. Cl.
CPC ............ *A61K 38/179* (2013.01); *A61K 47/12* (2013.01); *A61K 47/183* (2013.01); *A61K 47/26* (2013.01); *A61K 47/6811* (2017.08); *A61P 27/02* (2018.01)

(58) Field of Classification Search
CPC .. A61K 38/179; A61K 47/6811; C07K 14/71; C07K 2319/30
See application file for complete search history.

(56) References Cited

U.S. PATENT DOCUMENTS

| | | | |
|---|---|---|---|
| 8,216,575 B2 | 7/2012 | Yu | |
| 2017/0326106 A1* | 11/2017 | Zeitz | ................ A61K 9/0048 |
| 2019/0290725 A1* | 9/2019 | Vitti | ................ A61K 38/179 |
| 2021/0085745 A1* | 3/2021 | Innocenti | ............ C12Q 1/6883 |

OTHER PUBLICATIONS

Li et al. Safety and Efficacy of Conbercept in Neovascular Age-Related Macular Degeneration. Ophthalmology. 2014, vol. 121, pp. 1740-1747. (Year: 2014).*

* cited by examiner

*Primary Examiner* — Jeffrey E. Russel
(74) *Attorney, Agent, or Firm* — Lerner David LLP

(57) ABSTRACT

The present patent application provides methods for treating patients having angiogenic eye disorder by administering a VEGF antagonist, particularly an VEGF antagonist comprising the amino acid sequence of SEQ ID NO:1 in one or more treatment phases.

17 Claims, No Drawings

Specification includes a Sequence Listing.

SEQUENCE LISTING

```
<160> NUMBER OF SEQ ID NOS: 1

<210> SEQ ID NO 1
<211> LENGTH: 526
<212> TYPE: PRT
<213> ORGANISM: Artificial sequence
<220> FEATURE:
<223> OTHER INFORMATION: Sequence is synthesized

<400> SEQUENCE: 1

Gly Arg Pro Phe Val Glu Met Tyr Ser Glu Ile Pro Glu Ile Ile His
1               5                   10                  15

Met Thr Glu Gly Arg Glu Leu Val Ile Pro Cys Arg Val Thr Ser Pro
            20                  25                  30

Asn Ile Thr Val Thr Leu Lys Lys Phe Pro Leu Asp Thr Leu Ile Pro
        35                  40                  45

Asp Gly Lys Arg Ile Ile Trp Asp Ser Arg Lys Gly Phe Ile Ile Ser
    50                  55                  60

Asn Ala Thr Tyr Lys Glu Ile Gly Leu Leu Thr Cys Glu Ala Thr Val
65                  70                  75                  80

Asn Gly His Leu Tyr Lys Thr Asn Tyr Leu Thr His Arg Gln Thr Asn
                85                  90                  95

Thr Ile Ile Asp Val Val Leu Ser Pro Ser His Gly Ile Glu Leu Ser
            100                 105                 110

Val Gly Glu Lys Leu Val Leu Asn Cys Thr Ala Arg Thr Glu Leu Asn
        115                 120                 125

Val Gly Ile Asp Phe Asn Trp Glu Tyr Pro Ser Ser Lys His Gln His
    130                 135                 140

Lys Lys Leu Val Asn Arg Asp Leu Lys Thr Gln Ser Gly Ser Glu Met
145                 150                 155                 160

Lys Lys Phe Leu Ser Thr Leu Thr Ile Asp Gly Val Thr Arg Ser Asp
                165                 170                 175

Gln Gly Leu Tyr Thr Cys Ala Ala Ser Ser Gly Leu Met Thr Lys Lys
            180                 185                 190

Asn Ser Thr Phe Val Arg Val His Glu Lys Pro Phe Val Ala Phe Gly
        195                 200                 205

Ser Gly Met Glu Ser Leu Val Glu Ala Thr Val Gly Glu Arg Val Arg
    210                 215                 220

Ile Pro Ala Lys Tyr Leu Gly Tyr Pro Pro Glu Ile Lys Trp Tyr
225                 230                 235                 240

Lys Asn Gly Ile Pro Leu Glu Ser Asn His Thr Ile Lys Ala Gly His
                245                 250                 255

Val Leu Thr Ile Met Glu Val Ser Glu Arg Asp Thr Gly Asn Tyr Thr
            260                 265                 270

Val Ile Leu Thr Asn Pro Ile Ser Lys Glu Lys Gln Ser His Val Val
        275                 280                 285

Ser Leu Val Val Tyr Val Pro Pro Gly Pro Gly Asp Lys Thr His Thr
    290                 295                 300

Cys Pro Leu Cys Pro Ala Pro Glu Leu Leu Gly Gly Pro Ser Val Phe
```

```
305                 310                 315                 320
Leu Phe Pro Pro Lys Pro Lys Asp Thr Leu Met Ile Ser Arg Thr Pro
            325                 330                 335

Glu Val Thr Cys Val Val Asp Val Ser His Glu Asp Pro Glu Val
            340                 345                 350

Lys Phe Asn Trp Tyr Val Asp Gly Val Glu Val His Asn Ala Lys Thr
            355                 360                 365

Lys Pro Arg Glu Glu Gln Tyr Asn Ser Thr Tyr Arg Val Val Ser Val
    370                 375                 380

Leu Thr Val Leu His Gln Asp Trp Leu Asn Gly Lys Glu Tyr Lys Cys
385                 390                 395                 400

Lys Val Ser Asn Lys Ala Leu Pro Ala Pro Ile Glu Lys Thr Ile Ser
            405                 410                 415

Lys Ala Lys Gly Gln Pro Arg Glu Pro Gln Val Tyr Thr Leu Pro Pro
            420                 425                 430

Ser Arg Asp Glu Leu Thr Lys Asn Gln Val Ser Leu Thr Cys Leu Val
            435                 440                 445

Lys Gly Phe Tyr Pro Ser Asp Ile Ala Val Glu Trp Glu Ser Asn Gly
    450                 455                 460

Gln Pro Glu Asn Asn Tyr Lys Ala Thr Pro Pro Val Leu Asp Ser Asp
465                 470                 475                 480

Gly Ser Phe Phe Leu Tyr Ser Lys Leu Thr Val Asp Lys Ser Arg Trp
            485                 490                 495

Gln Gln Gly Asn Val Phe Ser Cys Ser Val Met His Glu Ala Leu His
            500                 505                 510

Asn His Tyr Thr Gln Lys Ser Leu Ser Leu Ser Pro Gly Lys
            515                 520                 525
```

METHOD FOR TREATING ANGIOGENIC EYE DISORDERS USING VEGF ANTAGONISTS

CROSS REFERENCE TO RELATED APPLICATIONS

This patent application claims the benefit of U.S. Prov. Ser. No. 63/040,850 filed Jun. 18, 2020, the disclosure of which is hereby incorporated herein by reference.

FIELD OF THE INVENTION

The present invention relates to the field of therapeutic treatments of eye disorders. More specifically, the invention relates to the administration of VEGF antagonists to treat eye disorders caused by or associated with angiogenesis.

BACKGROUND

VEGF stimulates division and proliferation of the endothelial cells, induces onset of neovascularization, and provides oxygen and nutrition to the tissue cells. While persistent angiogenesis might cause unexpected neovascularization, which may result in or exacerbate eye disorders such as age-related macular degeneration, diabetic retinopathy, diseases including tumor vascularization in various cancers, psoriasis and rheumatoid arthritis. Thus, inhibiting the angiogenic-promoting properties of VEGF appears to be an effective strategy for treating angiogenic eye disorders.

Several drugs have been approved by FDA for treatments of angiogenic eye disorders such as AMD, DME, mCNV and CRVO, include the administration of an anti-VEGF antibody called ranibizumab (Lucentis®, Genentech, Inc.) on a monthly basis by intravitreal injection; as well as aflibercept (Eylea®, Regeneron, Inc.) on a intravitreal injection every 4 weeks (approximately every 28 days, monthly) for the first 3 months, followed by intravitreal injection once every 8 weeks (2 months) for the treatment of AMD. Brolucizumab (BEOVU®, Novartis Pharms. corp.) was approved by FDA in October 2019, for the treatment of Neovascular (Wet) Age-Related Macular Degeneration (AMD). The recommended dose for Brolucizumab is 6 mg (0.05 mL of 120 mg/mL solution) administered by intravitreal injection monthly (approximately every 25-31 days) for the first three doses, followed by 6 mg (0.05 mL) by intravitreal injection once every 8-12 weeks.

Nonetheless, there remains a need in the art for new administration regimens for angiogenic eye disorders, especially those which allow for less frequent dosing or high level of efficacy. The present invention addresses this need.

Conbercept (KH902; Chengdu Kanghong Biotech Co., Ltd., Sichuan, China) was approved by the CFDA in November 2013, for the treatment of patients with neovascular (wet) age-related macular degeneration, with a recommended dose of 0.5 mg administered by intravitreal injection monthly for the first three months, followed by 0.5 mg administered by intravitreal injection once every three months. Conbercept is a recombinant soluble VEGF receptor fused with the second immunoglobulin (Ig) domain of VEGF receptor 1 (VEGFR1), the third and the fourth Ig domains of VEGFR2, and the Fc region of human IgG. Conbercept has a higher affinity with VEGF-A and all its isoforms by an additional fourth Ig domain of VEGFR2, which has been shown to be critical for the receptor dimerization and the enhancement of the association rate of VEGF to the receptor. In addition, conbercept can bind to P1GF, to which biologics of anti-VEGF has no binding activity.

BRIEF SUMMARY OF THE INVENTION

The present invention provides novel methods for treating angiogenic eye disorder (such as age-related macular degeneration (AMD), for example neovascular AMD) comprising administering a VEGF antagonist, particularly an VEGF antagonist comprising the amino acid sequence of SEQ ID NO:1 in one or more treatment phases. In some embodiments, there is provided a method for treating an angiogenic eye disorder in a human patient, said method comprising a first treatment phase comprising sequentially administering to the patient a VEGF antagonist at 4-week intervals on day 1, week 4 and week 8. In some embodiments, there is provided a method for treating an angiogenic eye disorder in a human patient, said method comprising a first treatment phase comprising sequentially administering to the patient a VEGF antagonist at 4-week intervals on day 1, week 4 and week 8, wherein the VEGF antagonist comprises amino acid sequence of SEQ ID NO:1. In some embodiments, the method further comprises a second treatment phase comprising administering to the patient the VEGF antagonist at 8 or 12 week intervals after the first three injections. In some embodiments, the second treatment phase immediately follows the first treatment phase. In some embodiments, the second treatment phase comprises administering to the patient the VEGF antagonist at 8-week intervals or 12-week intervals until about 36 weeks from the initiation of the treatment. In some embodiments, the second treatment phase comprises administering to the patient the VEGF antagonist at 8-week intervals. In some embodiments, the second treatment phase comprises administering to the patient a VEGF antagonist at 12-week intervals.

In some embodiments, the second treatment phase comprises administering to the patient the VEGF antagonist at 8-week intervals or 12-week intervals until about 36 weeks from the initiation of the treatment; and the method further comprises a third treatment phase, wherein the third treatment phase starts from week 40 and comprises administering the VEGF antagonist on a pro re nata (PRN) basis. In some embodiments, the total treatment cycle is about 92 weeks. In some embodiments, the second treatment phase comprises administering to the patient the VEGF antagonist at 8-week intervals. In some embodiments, the second treatment phase comprises administering to the patient a VEGF antagonist at 12-week intervals. In some embodiments, the dosing interval of the PRN is no less frequently than 12 weeks. In some embodiments, the dosing interval of the PRN is longer than 4 weeks but no less frequently than 12 weeks. In some embodiments, the dosing interval of the PRN is longer than 8 weeks but no less frequently than 12 weeks.

In some embodiments, the VEGF antagonist is administered to the patient by intravitreal administration. In some embodiments, the VEGF antagonist is administered to the patient at the dose of about 0.5 mg or 1 mg. In some embodiments, the VEGF antagonist is administered at the concentration of about 10 mg/mL. In some embodiments, the VEGF antagonist is administered at the concentration of about 20 mg/mL. In some embodiments, the injection volume of the VEGF antagonist is about 50 µl.

In some embodiments according to any one of the embodiments described above, the VEGF antagonist is intravitreally administered to the patient at the dose of 0.5 mg at the concentration of 10 mg/mL. In some embodiments, the VEGF antagonist is intravitreally administered to the patient at the dose of 1 mg at the concentration of 20 mg/mL. In some embodiments, the injection volume of the VEGF antagonist is about 50 µl.

In some embodiments according to any one of the embodiments described above, the patient has one or more of the following characteristics: i) has active subfoveal CNV lesions secondary to AMD evidenced by subfoveal FA leakage, or definite subfoveal fluid by SDOCT in the study eye at Screening; ii) has CNV that is at least 50% (e.g., at least about any of 60%, 60%, 70%, 80%, or more) of total lesion size in the study eye at Screening; or iii) has a ETDRS BCVA letter score of 78 to 25 in the study eye at Screening, including for example an ETDRS BCVA letter score of any of 78-70, 70-60, 60-50, 50-40, 40-30, or 30-25.

In some embodiments according to any one of the embodiments described above, the angiogenic eye disorder is selected from the group consisting of: age related macular degeneration, diabetic retinopathy, diabetic macular edema, central retinal vein occlusion, branch retinal vein occlusion, and corneal neovascularization.

In some embodiments according to any one of the embodiments described above, the patient has not been previously treated for the angiogenic eye disorder.

In some embodiments according to any one of the embodiments described above, the patient upon treatment has an improvement of BCVA score by at least about 9 letters, including for example at least about any of 10, 11, 12, 13, 14, 15, or more letters.

In some embodiments according to any one of the embodiments described above, the patient upon treatment has decrease in retinal thickness by at least about 80 µm, including for example at least about any of 90 µm, 100 µm, 110 µm, 120 µm, 130 µm, 140 µm, 150 µm, or more.

In some embodiments according to any one of the embodiments described above, the VEGF antagonist is in a formulation comprising sucrose, citrate, L-arginine and polysorbate 20. In some embodiments, the VEGF antagonist is in a formulation comprising 5% sucrose, 10 mM citrate, 100 mM L-arginine and 0.05% (w/v) polysorbate 20, at pH 7.7±0.3.

Other embodiments of the present invention will become apparent from a review of the ensuing detailed description.

DETAILED DESCRIPTION

The present application provides methods of treating angiogenic eye disorder (such as age-related macular degeneration (AMD), for example neovascular AMD) by administering a VEGF antagonist. An exemplary VEGF antagonist that can be used in the context of the present invention is a multimeric VEGF-binding protein comprising an immunoglobin-like (Ig) domain 2 of a first VEGF receptor and Ig domain 3 and 4 of a second VEGF receptor. In particular, VEGF antagonist is Conbercept, which has the amino acid sequence of SEQ ID NO:1.

In particular, the present application provides novel methods for treating angiogenic eye disorder (such as age-related macular degeneration (AMD), for example neovascular AMD) comprising administering a VEGF antagonist, particularly an VEGF antagonist comprising the amino acid sequence of SEQ ID NO:1 in one or more treatment phases. The first treatment phase comprises sequentially administering to the patient the VEGF antagonist at 4-week intervals on day 1, week 4 and week 8. The first phase may be immediately followed by a second treatment phase comprising administering to the patient the VEGF antagonist at 8 week (or 12 week) intervals after the first three injections, i.e., the first injection in the second phase would be 8 weeks (or 12 weeks) away from the last injection in the second dose, and subsequent injections in the second phase would be 8 weeks (or 12 weeks) from the immediate preceding dose. The second treatment phase may comprise administering to the patient the VEGF antagonist at 8-week intervals (or 12-week intervals) until about 36 weeks from the initiation of the treatment. Subsequently, the method may further comprise a third treatment phase, which can starts from week 40 and comprises administering the VEGF antagonist on a PRN basis. An exemplary treatment cycle can last about 92 weeks.

The methods of the present invention can particularly benefit patients having one or more of the following characteristics: i) has active subfoveal CNV lesions secondary to AMD evidenced by subfoveal FA leakage, or definite subfoveal fluid by SDOCT in the study eye at Screening; ii) has CNV that is at least 50% of total lesion size in the study eye at Screening; iii) has a ETDRS BCVA letter score of 78 to 25 in the study eye at Screening; 4) has not been previously treated for the angiogenic eye disorder.

The methods of the present invention are believed to be particularly effective in treating angiogenic eye disorder (such as age-related macular degeneration (AMD), for example neovascular AMD). For example, the patient upon treatment in some embodiments has an improvement of BCVA score by at least about 9 letters. In some embodiments, the patient upon treatment has a decrease in retinal thickness by at least about 80 µm.

The methods described herein can also be useful for any one of the following: 1) improving vision of a patent having an angiogenic eye disorder (such as AMD); 2) improving visual acuity of a patient having an angiogenic eye disorder (such as AMD); 3) decreasing retinal thickness in a patient having an antigogenic eye disorder (such as AMD); 4) preventing vision loss of a patent having an angiogenic eye disorder (such as AMD).

Unless defined otherwise, all technical and scientific terms used herein have the same meaning as commonly understood by one of ordinary skill in the art to which this invention belongs.

Although any methods and materials similar or equivalent to those described herein can be used in the practice or testing of the present invention, the preferred methods and materials are now described.

Dosing Regimens

The present invention provides methods for treating angiogenic eye disorder (such as age-related macular degeneration (AMD), for example neovascular AMD). The methods of the invention comprise sequentially administering to a patient multiple doses of a VEGF antagonist. As used herein, "sequentially administering" means that each dose of VEGF antagonist is administered to the patient at a different point in time, e.g., at different time separated by a predetermined interval (e.g., hours, days, weeks or months).

In some embodiments, the method comprises a first treatment phase comprising sequentially administering (e.g., via intravitreal administration) to the patient a VEGF antagonist (such as the VEGF antagonist comprising amino acid sequence of SEQ ID NO:1) at 4-week intervals on day 1, week 4 and week 8. In some embodiments, the method comprises a first treatment phase comprising sequentially administering (e.g., via intravitreal administration) to the patient a VEGF antagonist (such as the VEGF antagonist comprising amino acid sequence of SEQ ID NO:1) at 4-week intervals on day 1, week 4 and week 8, and a second treatment phase comprising administering (e.g., via intravitreal administration) to the patient the VEGF antagonist at 8 week intervals after the first three injections. In some embodiments, the second treatment phase immediately follows the first treatment phase, i.e., the first dose in the second phase is administered at 8 weeks following the last dose in the first phase. In some embodiments, the second treatment phase comprises administering to the patient the VEGF antagonist at 8-week intervals until about 36 weeks from the initiation of the treatment. In some embodiments, the second treatment phase comprises administering to the patient the VEGF antagonist at 8-week intervals until about 92 weeks from the initiation of the treatment. In some embodiments, the VEGF antagonist is administered to the patient at the dose of about 0.5 mg or 1 mg. In some embodiments, the VEGF antagonist is administered at the concentration of about 10 mg/mL. In some embodiments, the VEGF antagonist is administered at the concentration of about 20 mg/mL. In some embodiments, the injection volume of the VEGF antagonist is about 50 µl.

In some embodiments, the method comprises a first treatment phase comprising sequentially administering (e.g., via intravitreal administration) to the patient a VEGF antagonist (such as the VEGF antagonist comprising amino acid sequence of SEQ ID NO:1) at 4-week intervals on day 1, week 4 and week 8, and a second treatment phase comprising administering (e.g., via intravitreal administration) to the patient the VEGF antagonist at 12 week intervals after the first three injections. In some embodiments, the second treatment phase immediately follows the first treatment phase, i.e., the first dose in the second phase is administered at 12 weeks following the last dose in the first phase. In some embodiments, the second treatment phase comprises administering to the patient the VEGF antagonist at 12-week intervals until about 36 weeks from the initiation of the treatment. In some embodiments, the second treatment phase comprises administering to the patient the VEGF antagonist at 12-week intervals until about 92 weeks from the initiation of the treatment. In some embodiments, the VEGF antagonist is administered to the patient at the dose of about 0.5 mg or 1 mg. In some embodiments, the VEGF antagonist is administered at the concentration of about 10 mg/mL. In some embodiments, the VEGF antagonist is administered at the concentration of about 20 mg/mL. In some embodiments, the injection volume of the VEGF antagonist is about 50 µl.

In some embodiments, the method comprises a first treatment phase comprising sequentially administering (e.g., via intravitreal administration) to the patient a VEGF antagonist (such as the VEGF antagonist comprising amino acid sequence of SEQ ID NO:1) at 4-week intervals on day 1, week 4 and week 8, and a second treatment phase comprising administering (e.g., via intravitreal administration) to the patient the VEGF antagonist at 8 week intervals, wherein the first dose in the second phase is administered at 8 weeks following the last dose in the first phase, wherein the last dose in the second phase is at about 36 weeks from the initiation of the treatment, and the method further comprises a third treatment phase starting at week 40 and comprising administering (e.g., via intravitreal administration) the VEGF antagonist on a PRN basis. In some embodiments, the total treatment cycle is about 92 weeks. In some embodiments, the dosing interval of the PRN is no less frequently than 12 weeks. In some embodiments, the dosing interval of the PRN is longer than 4 weeks but no less frequently than 12 weeks. In some embodiments, the dosing interval of the PRN is longer than 8 weeks but no less frequently than 12 weeks. In some embodiments, the VEGF antagonist is administered to the patient at the dose of about 0.5 mg or 1 mg. In some embodiments, the VEGF antagonist is administered at the concentration of about 10 mg/mL. In some embodiments, the VEGF antagonist is administered at the concentration of about 20 mg/mL. In some embodiments, the injection volume of the VEGF antagonist is about 50 µl.

In some embodiments, the method comprises a first treatment phase comprising sequentially administering (e.g., via intravitreal administration) to the patient a VEGF antagonist (such as the VEGF antagonist comprising amino acid sequence of SEQ ID NO:1) at 4-week intervals on day 1, week 4 and week 8, and a second treatment phase comprising administering (e.g., via intravitreal administration) to the patient the VEGF antagonist at 12 week intervals, wherein the first dose in the second phase is administered at 12 weeks following the last dose in the first phase, wherein the last dose in the second phase is at about 36 weeks from the initiation of the treatment, and the method further comprises a third treatment phase starting at week 40 and comprising administering (e.g., via intravitreal administration) the VEGF antagonist on a PRN basis. In some embodiments, the total treatment cycle is about 92 weeks. In some embodiments, the dosing interval of the PRN is no less frequently than 12 weeks. In some embodiments, the dosing interval of the PRN is longer than 4 weeks but no less frequently than 12 weeks. In some embodiments, the dosing interval of the PRN is longer than 8 weeks but no less frequently than 12 weeks. In some embodiments, the VEGF antagonist is administered to the patient at the dose of about 0.5 mg or 1 mg. In some embodiments, the VEGF antagonist is administered at the concentration of about 10 mg/mL. In some embodiments, the VEGF antagonist is administered at the concentration of about 20 mg/mL. In some embodiments, the injection volume of the VEGF antagonist is about 50 µl.

In some embodiments according to any one of the embodiments described above, the VEGF antagonist is intravitreally administered to the patient at the dose of 0.5 mg at the concentration of 10 mg/mL. In some embodiments, the VEGF antagonist is intravitreally administered to the patient at the dose of 1 mg at the concentration of 20 mg/mL. In some embodiments, the injection volume of the VEGF antagonist is about 50 µl.

When the third treatment phase comprises dosing on PRN basis, the retreatment criteria can be based on one or more of the following: 1) new or persistent fluid based on OCT; 2) an increase in central retinal thickness of 100 microns or more as compared with the lowest previous value recorded; 3) a loss of 5 ETDRS letters or more from the best previous score recorded in conjunction with recurrent or persistent fluid on OCT; 4) new macular hemorrhage noted; or 5) maximum interval of 16 weeks has elapsed since the prior injection.

VEGF Antagonists

The methods of the present invention comprise administering to a patient a VEGF antagonist according to specified dosing regimens. As used herein, the expression "VEGF antagonist" means any molecule that blocks, reduces or interferes with the normal biological activity of VEGF.

VEGF antagonists include molecules which interfere with the interaction between VEGF and a natural VEGF receptor, e.g., molecules which bind to VEGF or a VEGF receptor and prevent or otherwise hinder the interaction between VEGF and a VEGF receptor. Specific exemplary VEGF antagonists include anti-VEGF antibodies, anti-VEGF receptor antibodies, and VEGF chimeric fusion protein.

As used herein, "VEGF" refers to vascular endothelial growth factor a sub-family of the platelet-derived growth factor family of cysteine-knot growth factors that are involved in both vasculogenesis (de novo formation of the embryonic circulatory system) and angiogenesis (the growth of blood vessels from pre-existing vasculature. All members of the VEGF family stimulate cellular responses by binding to tyrosine kinase receptors (VEGF receptors of VEGFRs) on the cell surface, causing them to dimerize and become activated. The VEGF receptors have an extracellular portion consisting of 7 immunoglobulin-like domains, a single transmembrane spanning region and an intracellular portion. VEGF-A binds to VEGFR-1 (Flt-1) and VEGFR-2 (KDR/Flk-1). VEGFR-2 appears to mediate almost all of the known cellular responses to VEGF.

As used herein, the terms "chimeric fusion protein" may be used interchangeably and refer to proteins comprising a fusion between two or more protein domains linked to a dimerizing or multimerizing domain (such as IgG Fc), wherein the soluble chimeric fusion protein targets two or more receptors or pathways related to angiogenesis. By domain is meant a part of protein sequence and structure that can function, and exist independently of the rest of the protein chain.

The terms "FLT-1" or "VEGFR1", as used herein, refer more specifically to a fms-like tyrosine kinase receptor, also known as vascular endothelial growth factor receptor 1.

The terms "KDR" or "FLK-1" or "VEGFR2", as used herein, refer more specifically to kinase insert domain-containing receptor or fetal liver kinase or vascular endothelial growth factor receptor 2.

As used herein, the term "immunoglobulin domain" refers to each of the independent and distinct domains that are found in the extracellular ligand region of the claimed soluble chimeric fusion proteins. The "immunoglobulin-like domain" refers to each of the seven independent and distinct domains that are found in the extracellular ligand-binding region of the Flt-1 and KDR receptors. Immunoglobulin domain are generally referred to by number The term "multimerizing domain" as used herein refers to a domain, such as the Fc domain from an IgG that is heterologous to the binding domains of the claimed soluble chimeric fusion proteins. A multimerizing domain may be essentially any polypeptide that forms a dimer (or higher order complex, such as a trimer, tetramer, etc.) with another polypeptide. Optionally, the multimerizing domain associates with other, identical multimerizing domains, thereby forming homomultimers.

In one exemplary embodiment of the present invention, the VEGF antagonist is a receptor-based chimeric molecule comprising an immunoglobin-like (Ig) domain 2 of VEGF receptor 1 and Ig domain 3 and 4 of VEGF receptor 2, and a multimerizing component.

The VEGF antagonist used in the Examples set forth herein below is a Conbercept, which is a recombinant soluble VEGF receptor fused with the second immunoglobulin (Ig) domain of VEGF receptor 1 (VEGFR1), the third and the fourth Ig domains of VEGFR2, and the Fc region of human IgG. The amino acid sequence of Conbercept is described in U.S. Pat. No. 8,216,575, which was named FP3'. FP3' has a total of 526 amino acids referred to SEQ ID NO: 8 in U.S. Pat. No. 8,216,575, herein referred to as SEQ ID NO:1.

Angiogenic Eye Disorders

The methods of the present invention can be used to treat any angiogenic eye disorder. The expression "angiogenic eye disorder," as used herein, means any disease of the eye which is caused by or associated with the growth or proliferation of blood vessels or by blood vessel leakage. Non-limiting examples of angiogenic eye disorders that are treatable using the methods of the present invention include age-related macular degeneration (e.g., wet AMD, exudative AMD, etc.), retinal vein occlusion (RVO), central retinal vein occlusion (CRVO; e.g., macular edema following CRVO), branch retinal vein occlusion (BRVO), diabetic macular edema (DME), choroidal neovascularization (CNV; e.g., myopic CNV), iris neovascularization, neovascular glaucoma, post-surgical fibrosis in glaucoma, proliferative vitreoretinopathy (PVR), optic disc neovascularization, corneal neovascularization, retinal neovascularization, vitreal neovascularization, pannus, pterygium, vascular retinopathy, and diabetic retinopathies.

In some embodiments, the patient has active subfoveal CNV lesions secondary to AMD evidenced by subfoveal FA leakage, or definite subfoveal fluid by SDOCT in the study eye at Screening.

In some embodiments, the patient has CNV that is at least 50% of total lesion size in the study eye at Screening. In some embodiments, the patient has at least about any of 60%, 60%, 70%, 80%, or more of total lesion size in the study eye at Screening.

In some embodiments, the patient has a ETDRS BCVA letter score of 78 to 25 in the study eye at Screening. In some embodiments, the patient has a ETDRS BCVA letter score of any of 78-70, 70-60, 60-50, 50-40, 40-30, or 30-25.

In some embodiments, the individual has received no previous treatment for neovascular AMD, including for example laser photocoagulation and/or photodynamic therapy (PDT) and/or IVT VEGF antagonists (treatment naïve). In some embodiments, the patient has not been previously treated for any of the angiogenic eye disorder to be treated with the methods described herein.

In some embodiments, the patient is about 18 to about 65 years old. In some embodiments, the patient is about 50 years or older, for example about any of 70, 75, 80, 85, 90, or older.

Pharmaceutical Formulations

The present invention includes methods in which the VEGF antagonist that is administered to the patient is contained within a pharmaceutical formulation. The pharmaceutical formulation may comprise the VEGF antagonist along with at least one inactive ingredient such as, e.g., a pharmaceutically acceptable carrier. Other agents may be incorporated into the pharmaceutical composition to provide improved transfer, delivery, tolerance, and the like. The term "pharmaceutically acceptable" means approved by a regulatory agency of the Federal or a state government or listed in the U.S. Pharmacopeia or other generally recognized pharmacopeia for use in animals, and more particularly, in humans. The term "carrier" refers to a diluent, adjuvant, excipient, or vehicle with which the antibody is administered. A multitude of appropriate formulations can be found in the formulary known to all pharmaceutical chemists: Remington's Pharmaceutical Sciences (15th ed, Mack Publishing Company, Easton, Pa., 1975)

Pharmaceutical formulations useful for administration by injection in the context of the present invention may be prepared by dissolving, suspending or emulsifying a VEGF antagonist in a sterile aqueous medium or an oily medium conventionally used for injections.

As the aqueous medium for injections, there are, for example, physiological saline, an isotonic solution containing sucrose and other auxiliary agents, etc., which may be used in combination with an appropriate solubilizing agent such as an alcohol (e.g., ethanol), a polyalcohol (e.g., propylene glycol, polyethylene glycol), a nonionic surfactant [e.g., polysorbate 80, HCO-50 (polyoxyethylene (50 mol) adduct of hydrogenated castor oil)], etc.

In some embodiments, the pharmaceutical composition comprises citrate. In some embodiments, the pharmaceutical composition comprises sucrose. In some embodiments, the pharmaceutical composition comprises polysorbate. In some embodiments, the VEGF antagonist is present in a pharmaceutical composition comprising sucrose, citrate, and polysorbate 20. In some embodiments, the VEGF antagonist is present in a pharmaceutical composition comprising 5% sucrose, 10 mM citrate, 100 mM L-arginine and 0.05% (w/v) polysorbate 20, at pH 7.7±0.3. In some embodiments, the VEGF antagonist in the pharmaceutical composition has a concentration of about 10 mg/mL. In some embodiments, the VEFG antagonist in the pharmaceutical composition has a concentration of about 20 mg/mL.

Modes of Administration

The VEGF antagonist (or pharmaceutical formulation comprising the VEGF antagonist) may be administered to the patient by any known delivery system and/or administration method. In certain embodiments, the VEGF antagonist is administered to the patient by ocular, intraocular, intravitreal or subconjunctival injection. In other embodiments, the VEGF antagonist is administered to the patient by topical administration, e.g., via eye drops or other liquid, gel, ointment or fluid which contains the VEGF antagonist and can be applied directly to the eye. Other possible routes of administration include, e.g., intradermal, intramuscular, intraperitoneal, intravenous, subcutaneous, intranasal, epidural, and oral.

Amount of VEGF Antagonist Administered

Each dose of VEGF antagonist administered to the patient over the course of the treatment regimen may contain the same, or substantially the same, amount of VEGF antagonist. Alternatively, the quantity of VEGF antagonist contained within the individual doses may vary over the course of the treatment regimen. For example, in certain embodiments, a first quantity of VEGF antagonist is administered in the initial dose, a second quantity of VEGF antagonist is administered in the secondary doses, and a third quantity of VEGF antagonist is administered in the tertiary doses. The present invention contemplates dosing schemes in which the quantity of VEGF antagonist contained within the individual doses increases over time (e.g., each subsequent dose contains more VEGF antagonist than the last), decreases over time (e.g., each subsequent dose contains less VEGF antagonist than the last), initially increases then decreases, initially decreases then increases, or remains the same throughout the course of the administration regimen.

The amount of VEGF antagonist administered to the patient in each dose is, in most cases, a therapeutically effective amount. As used herein, the phrase "therapeutically effective amount" means a dose of VEGF antagonist that results in a detectable improvement in one or more symptoms or indicia of an angiogenic eye disorder, or a dose of VEGF antagonist that inhibits, prevents, lessens, or delays the progression of an angiogenic eye disorder. In the case of an anti-VEGF antibody or a VEGF receptor-based chimeric molecule such as conbercept, a therapeutically effective amount can be from about 0.05 mg to about 2 mg, e.g., about 0.05 mg, about 0.1 mg, about 0.15 mg, about 0.2 mg, about 0.25 mg, about 0.3 mg, about 0.35 mg, about 0.4 mg, about 0.45 mg, about 0.5 mg, about 0.55 mg, about 0.6 mg, about 0.65 mg, about 0.7 mg, about 0.75 mg, about 0.8 mg, about 0.85 mg, about 0.9 mg, about 1.0 mg, about 1.05 mg, about 1.1 mg, about 1.15 mg, about 1.2 mg, about 1.25 mg, about 1.3 mg, about 1.35 mg, about 1.4 mg, about 1.45 mg, about 1.5 mg, about 1.55 mg, about 1.6 mg, about 1.65 mg, about 1.7 mg, about 1.75 mg, about 1.8 mg, about 1.85 mg, about 1.9 mg, about 2.0 mg.

In some embodiments, the VEGF antagonist is administered at the dose of 0.5 mg per injection. In some embodiments, the VEGF antagonist is administered at the dose of 1.0 mg per injection. In some embodiments, the concentration of the VEGF antagonist is administered (e.g., by intravitreal injection) at 0.5 mg dose at the concentration of 10 mg/mL. In some embodiments, the VEGF antagonist is administered at 1.0 mg dose at the concentration of 20 mg/mL.

Evaluation of Treatment

The methods of the present invention are useful for treating angiogenic eye disorders (such as Neovascular Age-related Macular Degeneration) in patients that have been diagnosed with or are at risk of being afflicted with an angiogenic eye disorder. In one exemplary embodiment, the methods of the present invention demonstrate efficacy within 96 weeks of the initiation of the treatment regimen (with the initial dose administered at "week 0"), e.g., by the end of week 12, by the end of week 36, by the end of week 40, by the end of week 96 etc.

In the context of methods for treating angiogenic eye disorders such as AMD, CRVO, and DME, the efficacy can be evaluated by the change from baseline in best corrected visual acuity (BCVA) by Early Treatment of Diabetic Retinopathy Study (ETDRS) method, or the mean change from baseline in central retinal thickness (μm) by SD-OCT.

In some embodiments according to any one of the embodiments described above, the patient upon treatment has an improvement of BCVA score by at least about 5 letters, including for example at least about any of 6, 7, 8, 9, 10, 11, 12, 13, 14, 15, 16, 17, 18, 19, 20, or more letters. In some embodiments, the BCVA score is calculated by using Early Treatment of Diabetic Retinopathy Study (ETDRS) method. In some embodiments according to any one of the embodiments described above, the patient upon treatment has a decrease in BCVA score by no more than 15 letters, including for example no more than about any of 14, 13, 12, 11, 10, 9, 8, 7, 6, 5, 4, 3, 2, or 1 letters. In some embodiments, the BCVA score is calculated by using Early Treatment of Diabetic Retinopathy Study (ETDRS) method. In some embodiments, the assessment is done at the end of the second treatment phase. In some embodiments, the assessment is done at the end of the entire treatment cycle. In some embodiments, the assessment is done at the end of week 12, at the end of week 36, at the end of week 40, at the end of week 48, or at the end of week 96.

In some embodiments according to any one of the embodiments described above, the patient upon treatment has a decrease in retinal thickness by at least about 80 μm, including for example at least about any of 90 μm, 100 μm, 110 μm, 120 μm, 130 μm, 140 μm, 150 μm, or more. Retinal thickness can be assessed, for example, by SD-OCT or imaging. In some embodiments, the assessment is done at the end of the second treatment phase. In some embodiments, the assessment is done at the end of the entire treatment cycle. In some embodiments, the assessment is done at the end of the entire treatment cycle. In some embodiments, the assessment is done at the end of week 12, at the end of week 36, at the end of week 40, at the end of week 48, or at the end of week 96.

The patient can also be evaluated change in CRT on optical coherence tomography (OCT) imaging, change in leakage area on fluorescein angiography (FA) imaging over time, and incidence rate of adverse events (AE) over time. Visual function assessment, intraocular pressure measurements, slit-lamp examinations, imaging with color fundus photography (CFP), OCT, and FA can all be conducted.

EXAMPLES

The following examples are put forth so as to provide those of ordinary skill in the art with a complete disclosure and description of how to make and use the methods and compositions of the invention, and are not intended to limit the scope of what the inventors regard as their invention. Efforts have been made to ensure accuracy with respect to numbers used (e.g., amounts, temperature, etc.) but some experimental errors and deviations should be accounted for. Unless indicated otherwise, parts are parts by weight, molecular weight is average molecular weight, temperature is in degrees Centigrade, and pressure is at or near atmospheric.

The exemplary VEGF antagonist used in all Examples set forth below is a conbercept as described before. For purposes of the following Examples, "monthly" dosing is equivalent to dosing once every four weeks.

Example 1

Phase III Efficacy and Safety Trial of Conbercept Intravitreal Injection for Neovascular Age-Related Macular Degeneration A. Objectives, Hypotheses and Endpoints Two parallel Phase III clinical trials were carried out to investigate the use of VEGF trap to treat patients with the neovascular form of age-related macular degeneration (PANDA-1 and PANDA-2).

The purpose of this clinical study is to evaluate the efficacy and safety of two different levels of conbercept intravitreal (IVT) injection as compared to the approved vascular endothelial growth factor (VEGF) antagonist active control, aflibercept intravitreal injection (2.0 mg/eye, Eylea®), in subjects with neovascular AMD.

The primary objective of this study is to determine if 0.5 mg or 1.0 mg conbercept is non-inferior to aflibercept 2.0 mg as measured by the change from baseline in best corrected visual acuity (BCVA) by Early Treatment of Diabetic Retinopathy Study (ETDRS) method at the Week 36 visit.

The primary endpoint is the mean change from baseline in best corrected visual acuity (BCVA) by Early Treatment of Diabetic Retinopathy Study (ETDRS) method at Week 36 in the study eye.

The secondary objectives of this study are:
a) To evaluate the difference in efficacy between conbercept doses and aflibercept; b) To compare the safety and tolerability of conbercept doses and aflibercept, and to evaluate the pharmacokinetics and immunogenicity of conbercept doses, when feasible.

The secondary Outcome Measures are as follows:
1. Proportion of subjects maintaining vision (i.e., losing <15 ETDRS BCVA letters) from baseline to Week 36 [Time Frame: Baseline to Week 36]
2. Proportion of subjects gaining ≥15 ETDRS BCVA letters from baseline to Week 36 [Time Frame: Baseline to Week 36]
3. Mean change from baseline in central retinal thickness (μm) by spectral domain optical coherence tomography (SD-OCT) at Week 36 [Time Frame: Baseline and Week 36]
4. Proportion of subjects maintaining vision (i.e. losing <15 ETDRS BCVA letters) from baseline to Week 48 [Time Frame: Baseline to Week 48]
5. Mean change from baseline in ETDRS BCVA letter score at Week 96 [Time Frame: Baseline and Week 96]
6. Number of participants with adverse events as measure of safety and tolerability [Time Frame: Baseline to Week 96]
7. Blood concentration of conbercept doses conducted in a subgroup of subjects, when feasible [Time Frame: Baseline to Week 96]
8. Half-life (t½) of conbercept doses conducted in a subgroup of subjects, when feasible [Time Frame: Baseline to Week 96]
9. Presence of anti-drug antibody of conbercept doses conducted in a subgroup of subjects, when feasible [Time Frame: Baseline to Week 96]

B. Study Design

PANDA-1:

This study will randomize approximately 1140 subjects in a ratio of 1:1:1 to receive IVT injections of 0.5 mg conbercept, 1.0 mg conbercept, or 2.0 mg aflibercept.

Biological: 0.5 mg Conbercept Intravitreal Injection
Subjects received 0.5 mg conbercept intravitreal injection at Day 1, Week 4 and Week 8 (three injection loading dose), and treated every eight weeks thereafter (0.5 mg, q8w) for a total of 92 weeks treatment in the study eye.

Biological: 1.0 mg Conbercept Intravitreal Injection
Subjects received 1.0 mg conbercept intravitreal injection at Day 1, Week 4 and Week 8 (three injection loading dose), and treated every twelve weeks thereafter (1.0 mg, q12w) for a total of 92 weeks treatment in the study eye.

Biological: 2.0 mg Aflibercept Intravitreal Injection
Subjects received 2.0 mg aflibercept intravitreal injection at Day 1, Week 4 and Week 8 (three injection loading dose), and treated every eight weeks thereafter (2.0 mg, q8w) for a total of 92 weeks of treatment in the study eye.

PANDA-2:

This study will randomize approximately 1140 subjects in a ratio of 1:1:1 to receive IVT injections of 0.5 mg conbercept, 1.0 mg conbercept, or 2.0 mg aflibercept.

Biological: 0.5 mg Conbercept Intravitreal Injection
Subjects received 0.5 mg conbercept intravitreal injection at Day 1, Week 4 and Week 8 (three injection loading dose), and treated every eight weeks thereafter (0.5 mg, q8w) through Week 36. At the Week 40 visit, the criteria-based pro re nata (PRN) approach will begin through the end of the treatment period at Week 92, for a total of 92 weeks treatment in the study eye.

Biological: 1.0 mg Conbercept Intravitreal Injection
Subjects received 1.0 mg conbercept intravitreal injection at Day 1, Week 4 and Week 8 (three injection loading dose), and treated every twelve weeks thereafter (1.0 mg, q12w) through Week 36. At the Week 40 visit, the criteria-based PRN approach will begin through the end of the treatment period at Week 92, for a total of 92 weeks treatment in the study eye.

Biological: 2.0 mg Aflibercept Intravitreal Injection

Subjects received 2.0 mg aflibercept intravitreal injection at Day 1, Week 4 and Week 8 (three injection loading dose), and treated every eight weeks thereafter (2.0 mg, q8w) through Week 36. At the Week 40 visit, the criteria-based PRN approach will begin through the end of the treatment period at Week 92, for a total of 92 weeks treatment in the study eye.

All subjects will receive sham procedure at visit intervals between each scheduled IVT injection to mask any differences in dosing frequency.

Summary of Visit Schedule:

Subjects will be examined at Screening (≤14 days prior to first injection), on the day of treatment initiation (baseline), and every 4 weeks thereafter for the duration of the study.

All subjects will be followed for a total of 92 weeks of study medication treatment and 96 weeks of evaluation overall.

Study Population Characteristics

Number of Randomized Subjects:

Approximately 1,140 subjects, 380 per arm, with a target of 340 subjects who complete their assigned treatment for each study arm to the Week 26 visit and a target of 320 subjects in each study arm to complete the study at week 96.

Study Eye:

The study eye will be defined as the eye meeting all of the inclusion criteria and none of the exclusion criteria. If both eyes meet the enrollment criteria, then the study eye will be defined as the eye with the lower ETDRS BCVA letter score at the time of randomization. If both eyes have the same ETDRS BCVA letter score and meet all enrollment criteria at randomization, the Investigator will determine the study eye.

Criteria

Inclusion Criteria:
1. Men and women ≥50 years of age at the Screening visit;
2. Females must be at least 1 year postmenopausal, or surgically sterilized, or, if of childbearing potential, must have a negative pregnancy test at the Screening visit;
   Women of childbearing potential must agree to use a highly effective method of contraception throughout the study.
3. Have received no previous treatment for neovascular AMD, including laser photocoagulation and/or photodynamic therapy (PDT) and/or IVT VEGF antagonists (treatment naïve) and;
4. Have active subfoveal choroidal neovascularization (CNV) lesions secondary to AMD (including polypoidal choroidal vasculopathy (PCV)) evidenced by subfoveal fluorescein angiography (FA) leakage, or definite subfoveal fluid by SD-OCT in the study eye at Screening;
5. Have a ETDRS BCVA letter score of 78 to 25 in the study eye at Screening;
6. Are willing and able to sign the study written informed consent form (ICF).

Exclusion Criteria:
1. Have had any prior ocular or systemic treatment (investigational or approved) or surgery for the treatment of neovascular AMD in the study eye except dietary supplements or vitamins;
2. Have participated as a subject in any interventional clinical trial within one month (30 days) prior to Baseline visit;
3. Have a subretinal hemorrhage that is either 50% or more of the total lesion area, or blood is under the fovea and is one or more disc areas in size (greater than 2.5 mm2) in the study eye at Screening;
4. Have any retinal pigment epithelial tears or rips in the study eye at Screening or upon examination at Baseline;
5. Have any vitreous hemorrhage in the study eye upon examination at Baseline or history of vitreous hemorrhage within eight weeks prior to Screening;
6. Have any other cause of CNV;
7. Have had prior pars plana vitrectomy in the study eye;
8. Have presence of a full thickness macular hole at Screening or upon examination at Baseline or a history of a full thickness macular hole in the study eye;
9. Have prior trabeculectomy or other filtration surgery in the study eye;
10. Have uncontrolled glaucoma;
11. Have active intraocular inflammation in either eye at Screening or upon examination at Baseline or a history of uveitis in either eye;
12. Have aphakia or pseudophakia with absence of posterior capsule (unless it occurred as a result of yttrium aluminum garnet (YAG) posterior capsulotomy) in the study eye.
13. Significant media opacities, including cataract, in the study eye that, in the opinion of the Investigator, could require either medical or surgical intervention during the study period;
14. Have any use of long acting intraocular steroids, including implants, within six months prior to Day 1, Baseline;
15. Have any known allergy to povidone iodine or known serious allergy to the fluorescein sodium for injection in angiography;
16. Any history of known contraindications indicated in the Food and Drug Administration (FDA)-approved label for the active control;
17. If female, be pregnant (positive urine pregnancy test at Screening) or breastfeeding.

Evaluation Criteria

Efficacy Measures:

BCVA as measured by ETDRS procedure with manifest refraction.

Retinal thickness and anatomy and lesion characteristics as measured by SD-OCT and imaging modalities Safety Measures:

Adverse event reporting

Slit-lamp biomicroscopy

IOP

Dilated indirect ophthalmoscopy

SD-OCT

Laboratory analyses of blood and urine

Immunogenicity to conbercept in serum (sub-group)

Specular microscopy (sub-group)

Urine pregnancy testing at Screening

Other:

Patient-reported outcome: NEI-VFQ-25

Pharmacokinetics of conbercept (sub-group), where feasible

The retreatment criteria for this protocol beginning at Week 40 and to be assessed at each visit through the Week 92 visit are as follows:

New or persistent fluid based on OCT; or

An increase in central retinal thickness of 100 microns or more as compared with the lowest previous value recorded; or A loss of 5 ETDRS letters or more from the best previous score recorded in conjunction with recurrent or persistent fluid on OCT; or New macular hemorrhage noted; or A maximum interval of 16 weeks has elapsed since the prior injection

I claim:

1. A method for treating an angiogenic eye disorder in a human patient, said method comprising a first treatment phase comprising sequentially administering to the patient a VEGF antagonist at 4-week intervals on Day 1, Week 4 and Week 8; wherein the VEGF antagonist comprises amino acid sequence of SEQ ID NO:1, further comprising a second treatment phase, the second treatment phase comprises administering to the patient the VEGF antagonist at 8-week intervals or 12-week intervals until about 36 weeks from the initiation of the treatment, and comprising a third treatment phase, wherein the third treatment phase starts from week 40 and comprises administering the VEGF antagonist on a PRN basis; wherein upon treatment the patient has a decrease in retinal thickness by at least about 80 μm.

2. The method according to claim 1, wherein the second treatment phase comprises administering to the patient the VEGF antagonist at 8-week intervals.

3. The method according to claim 1, wherein the second treatment phase comprises administering to the patient the VEGF antagonist at 12-week intervals.

4. The method according to claim 1, wherein a dosing interval of the PRN is no less frequently than 12 weeks.

5. The method according to claim 1, wherein a dosing interval of the PRN is longer than 4 weeks but no less frequently than 12 weeks.

6. The method according to claim 1, wherein a dosing interval of the PRN is longer than 8 weeks but no less frequently than 12 weeks.

7. The method according to claim 1, wherein the VEGF antagonist is administered to the patient by intravitreal administration.

8. The method according to claim 1, wherein the dose of the VEGF antagonist is about 0.5 mg or 1 mg.

9. The method according to claim 8, wherein the concentration of the VEGF antagonist administered to the patient is 10 mg/mL for the 0.5 mg dose.

10. The method according to claim 8, wherein the concentration of the VEGF antagonist administered to the patient is 20 mg/mL for the 1 mg dose.

11. The method according to claim 1, wherein the injection volume of the VEGF antagonist is about 50 μl.

12. The method according to claim 1, wherein of the patient has one or more of the following characteristics:
 i) has active subfoveal CNV lesions secondary to AMD evidenced by subfoveal FA leakage, or definite subfoveal fluid by SDOCT in the study eye at Screening;
 ii) has CNV that is at least 50% of total lesion size in the study eye at Screening; or
 iii) has a ETDRS BCVA letter score of 78 to 25 in the study eye at Screening.

13. The method according to claim 1, wherein the angiogenic eye disorder is selected from the group consisting of: age related macular degeneration, diabetic retinopathy, diabetic macular edema, central retinal vein occlusion, branch retinal vein occlusion, and corneal neovascularization.

14. The method according to claim 1, wherein the patient has not been previously treated for the angiogenic eye disorder.

15. The method according to claim 1, wherein upon treatment the patient has an improvement of BCVA score by at least about 9 letters.

16. The method according to claim 1, wherein the VEGF antagonist is in a formulation comprising sucrose, citrate, L-arginine and polysorbate.

17. The method according to claim 16, wherein the VEGF antagonist is in a formulation comprising 5 weight % sucrose, 10 mM citrate, 100 mM L-arginine and 0.05% (w/v) polysorbate 20, at pH 7.7±0.3.

* * * * *